US010201339B2

(12) United States Patent
Raybin et al.

(10) Patent No.: US 10,201,339 B2
(45) Date of Patent: Feb. 12, 2019

(54) TRIPLE PRONGED CLIP

(71) Applicant: BOSTON SCIENTIFIC SCIMED, INC., Maple Grove, MN (US)

(72) Inventors: Samuel Raybin, Marlborough, MA (US); Paul Smith, Smithfield, RI (US); Naroun Suon, Lawrence, MA (US); John B. Golden, Norton, MA (US); Bernard Barrosse Schwartz, East Dorset, VT (US); Kevin Scott Gell, Roxbury Crossing, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 395 days.

(21) Appl. No.: 15/012,393

(22) Filed: Feb. 1, 2016

(65) Prior Publication Data

US 2016/0228108 A1    Aug. 11, 2016

Related U.S. Application Data

(60) Provisional application No. 62/112,411, filed on Feb. 5, 2015.

(51) Int. Cl.
*A61B 17/08* (2006.01)
*A61D 1/00* (2006.01)
(Continued)

(52) U.S. Cl.
CPC .......... *A61B 17/0057* (2013.01); *A61B 1/018* (2013.01); *A61B 17/083* (2013.01);
(Continued)

(58) Field of Classification Search
CPC ..... A61B 17/08; A61B 17/081; A61B 17/083; A61B 17/088; A61B 17/0057;
(Continued)

(56) References Cited

U.S. PATENT DOCUMENTS

| 5,976,161 | A | 11/1999 | Kirsch et al. | |
| 2011/0077668 | A1* | 3/2011 | Gordon | A61B 17/0057 606/142 |
| 2015/0057704 | A1 | 2/2015 | Takahashi et sl. | |

FOREIGN PATENT DOCUMENTS

| EP | 2 127 606 | 12/2009 |
| EP | 2 361 561 | 8/2011 |
| WO | 2014/034254 | 3/2014 |

* cited by examiner

*Primary Examiner* — Melanie R Tyson
(74) *Attorney, Agent, or Firm* — Fay Kaplun & Marcin, LLP

(57) ABSTRACT

A device for treating tissue includes a capsule extending longitudinally from a proximal end to a distal end and including a lumen extending therein and a clip slidably received within the lumen of the capsule. The clip includes a middle prong, a first outer prong and a second outer prong. The first prong is coupled to the middle prong so that the first prong is movable relative to the middle prong between a first open configuration and a first closed configuration. The second outer prong coupled to the middle prong so that the second prong is movable relative to the middle prong between a second open configuration and a second closed configuration. The first and second outer prongs are independently movable relative to the middle prong to be moved between the first and second open configurations to the first and second open configurations and the first and second closed configurations.

10 Claims, 8 Drawing Sheets

(51) Int. Cl.
*A61B 17/00* (2006.01)
*A61B 17/122* (2006.01)
*A61B 17/128* (2006.01)
*A61B 1/018* (2006.01)
*A61B 17/10* (2006.01)

(52) U.S. Cl.
CPC ............ *A61B 17/10* (2013.01); *A61B 17/122* (2013.01); *A61B 17/1285* (2013.01); *A61B 17/1227* (2013.01); *A61B 2017/0034* (2013.01); *A61B 2017/00575* (2013.01); *A61B 2017/00584* (2013.01); *A61B 2017/00818* (2013.01)

(58) Field of Classification Search
CPC .............. A61B 17/122; A61B 17/1227; A61B 17/1285; A61B 2017/081; A61B 2017/00575; A61B 2017/00579; A61B 2017/00584; A61B 2017/00592
USPC .................................................. 606/151, 213
See application file for complete search history.

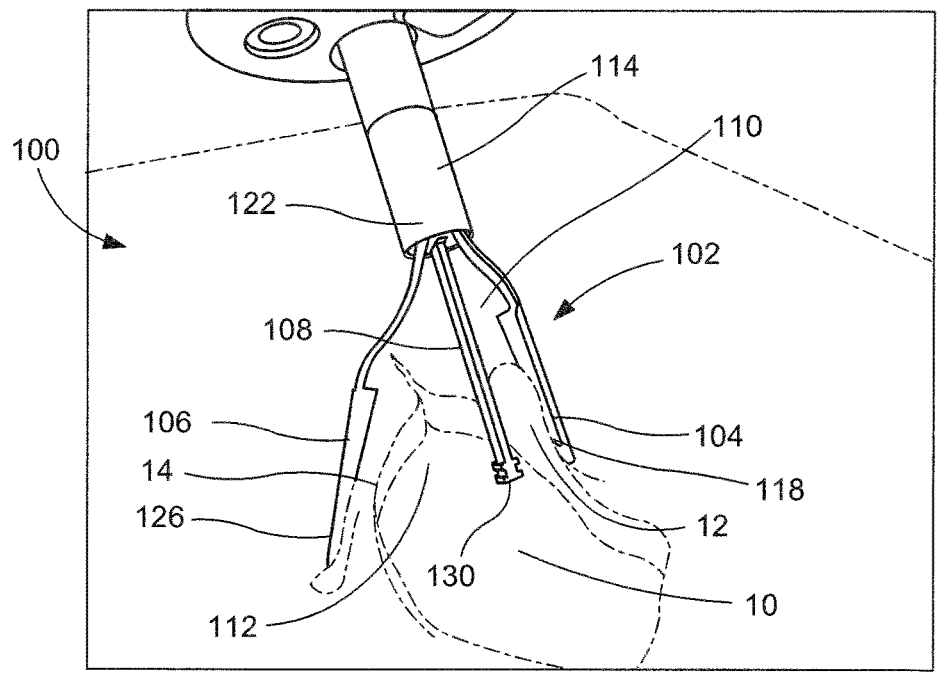
F I G. 1
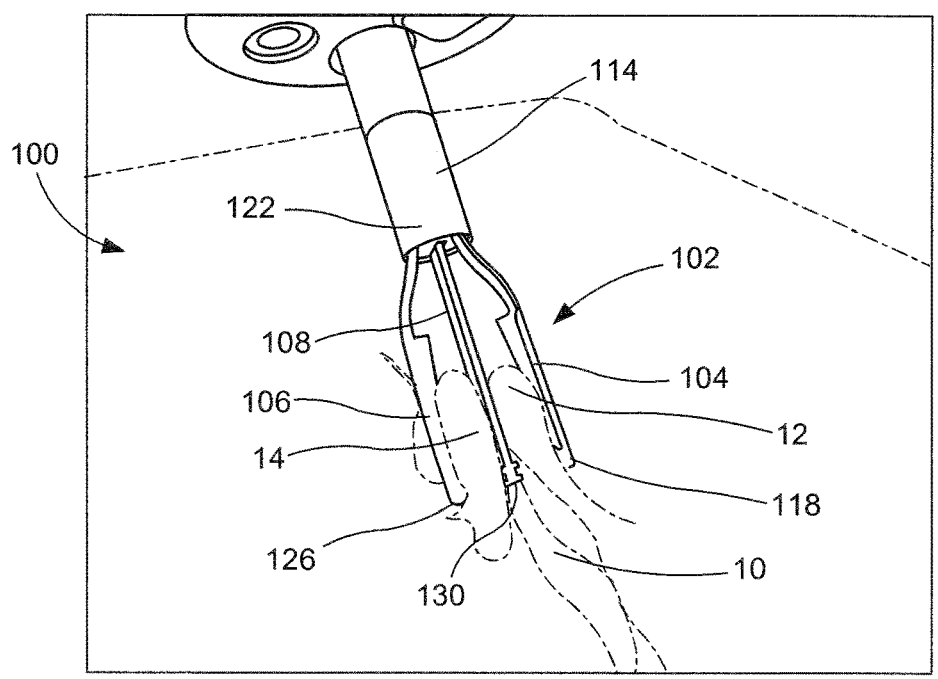
F I G. 2

TRIPLE PRONGED CLIP

PRIORITY CLAIM

This application claims priority to U.S. Provisional Patent Application Ser. No. 62/112,411 filed Feb. 5, 2015; the disclosure of which is incorporated herewith by reference.

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may entail an increased risk that the wall of the GI tract will be perforated, or may require closure of one or more openings intentionally formed in the GI tract wall as part of the procedure. Endoscopic closure reduces cost and may reduce the trauma and inconvenience associated with these procedures. However, conventional tissue closure devices may be insufficient to close certain perforations.

SUMMARY

The present disclosure is directed to a device for treating tissue, comprising a capsule extending longitudinally from a proximal end to a distal end and including a lumen extending therein and a clip slidably received within the lumen of the capsule. The clip includes a middle prong, a first outer prong coupled to the middle prong so that the first prong is movable relative to the middle prong between a first open configuration, in which distal ends of the first and middle prongs are separated from one another to receive a first portion of tissue therebetween, and a first closed configuration, in which the distal end of the first prong is moved toward the distal end of the middle prong to grip the first portion of tissue therebetween, and a second outer prong coupled to the middle prong so that the second prong is movable relative to the middle prong between a second open configuration, in which distal ends of the second and middle prongs are separated from one another to receive a second portion of tissue therebetween, and a second closed configuration, in which the distal end of the second prong is moved toward the distal end of the middle prong to grip the second portion of tissue therebetween, the first and second outer prongs independently movable relative to the middle prong to be moved between the first and second open configurations to the first and second open configurations and the first and second closed configurations, wherein the first and second prongs are biased toward the first and second open configurations, respectively, so that, when the clip is drawn proximally into the capsule, the first and second prongs are constrained toward the first and second closed configurations via an interior surface of the capsule.

In an embodiment, the middle prong may be releasably coupled to the first and second prongs.

In an embodiment, the first prong may include a first shoulder positioned therealong so that, when the first shoulder engages the interior surface of the capsule the first prong is constrained toward the first closed configuration, and the second prong includes a second shoulder positioned therealong so that, when the second shoulder engages the interior surface of the capsule the second prong is constrained toward the second closed configuration, the second shoulder positioned distally of the first shoulder so that when the clip is moved proximally relative to the capsule, the clip is moved to the first closed configuration prior to the second closed configuration.

In an embodiment, the distal end of the capsule may include a longitudinal recess extending therealong, the recess aligned with the second prong so that, when the clip and the capsule are moved longitudinally relative to one another toward the first and second closed configurations, the first prong engages the interior surface of the capsule before the second prong.

In an embodiment, the device may further comprise a control element coupled to the proximal end of the middle prong for moving the clip between the first and second open configurations and the first and second closed configurations.

In an embodiment, one of the first and second prongs may include an engaging element for engaging a corresponding engaging element of the capsule when the middle prong is disengaged therefrom to lock the first and second prongs within the capsule in the first and second closed configurations.

In an embodiment, the control element may be releasably coupled to the middle prong.

In an embodiment, the lumen of the capsule may include an enlarged portion at a distal end therefrom, the enlarged portion sized and shaped to receive one of the first and second prongs in one of the first and second open configurations, respectively, and to prevent receipt of the middle prong therein, the capsule rotatable about a longitudinal axis thereof relative to the clip to move the clip between the first and second open configurations and the first and second closed configurations.

In an embodiment, distal ends of at least one of the first, second and middle prongs may include tissue gripping structures.

In an embodiment, the first, second and middle prongs may be connected to one another via a connecting element, the middle prong fixed relative to the connecting element, the first prong pivotally coupled thereto via a first pivoting point and the second prong pivotally coupled thereto via a second pivoting point.

In an embodiment, a proximal end of the first prong may be connected to a first control member and a proximal end of the second prong is connected to a second control member, the first and second control members being independently actuatable.

The present disclosure is also directed to a clipping system, comprising a capsule extending longitudinally from a proximal end to a distal end and including a lumen extending therethrough along with a clip including a middle prong, a first outer prong and a second outer prong, proximal ends of the middle, first and second prongs received within the lumen of the capsule, the first prong biased toward a first open configuration in which distal ends of the first and middle prongs are separated from one another, the second prong biased toward a second open configuration in which distal ends of the second and middle prongs are separated from one another and a first actuating member slidably received within the lumen of the capsule and longitudinally movable between a first position, in which a distal end of the first actuating member is proximal a distal portion of the first prong so that the first prong is in the first open configuration, and a second position, in which the first actuating member is moved distally over the distal portion of the first prong to move the first prong toward the middle prong in a first closed configuration in combination with a second actuating member slidably received within the lumen of the capsule and longitudinally movable between a first position, in which a distal end of the second actuating member is proximal a distal portion of the second prong so that the second prong is in the second open configuration, and a second position, in which the second actuating member is moved distally over the distal portion of the second prong to move the second prong toward the middle prong in a second closed configuration, the first and second actuating members being independently movable.

In an embodiment, the distal portions of each of the first and second prongs may include a curved exterior surface for engaging the first and second actuating members, respectively.

In an embodiment, each of the first and second actuating members may include a locking element for locking the first and second actuating members over the distal portions of the first and second prongs, respectively.

In an embodiment, the locking element may include a tab biased laterally outward to engage the distal end of the capsule when the tab is moved distally therebeyond.

The present disclosure is also directed to a method for treating a tissue, comprising inserting a clipping device through a working channel of an endoscope to a target site within a patient body, the clipping device including a capsule and a clip slidably housed therein, moving the clip distally relative to the capsule so a first outer prong is permitted to revert to a biased first open configuration in which a distal end of the first outer prong is separated from a distal end of a middle prong and a second outer prong is permitted to revert to a biased second open configuration in which a distal end of the second outer prong is separated from the distal end of the middle prong, wherein the clip is moved longitudinally relative to the capsule via a control element coupled to a proximal end of the middle prong, positioning the clipping device over a first portion of tissue along a first side of a tissue defect and drawing the clip proximally relative to the capsule so that the first prong is constrained by an interior surface of the capsule toward the middle prong to a first closed configuration in which the first portion of tissue is gripped between the distal ends of the first prong and the middle prong, and positioning the clipping device over a second portion of tissue along a second side of the tissue defect opposite the first and drawing the clip further proximally relative to the capsule so that the second prong is constrained by the interior surface of the capsule toward the second closed configuration toward the middle prong to a second closed configuration in which the second tissue portion is gripped between the distal ends of the second prong and the middle prong.

BRIEF DESCRIPTION

FIG. 1 shows a perspective view of a device according to a first exemplary embodiment of the present disclosure, in a first configuration;

FIG. 2 shows a perspective view of the device of FIG. 1, in a second configuration;

DETAILED DESCRIPTION

Figure 3:
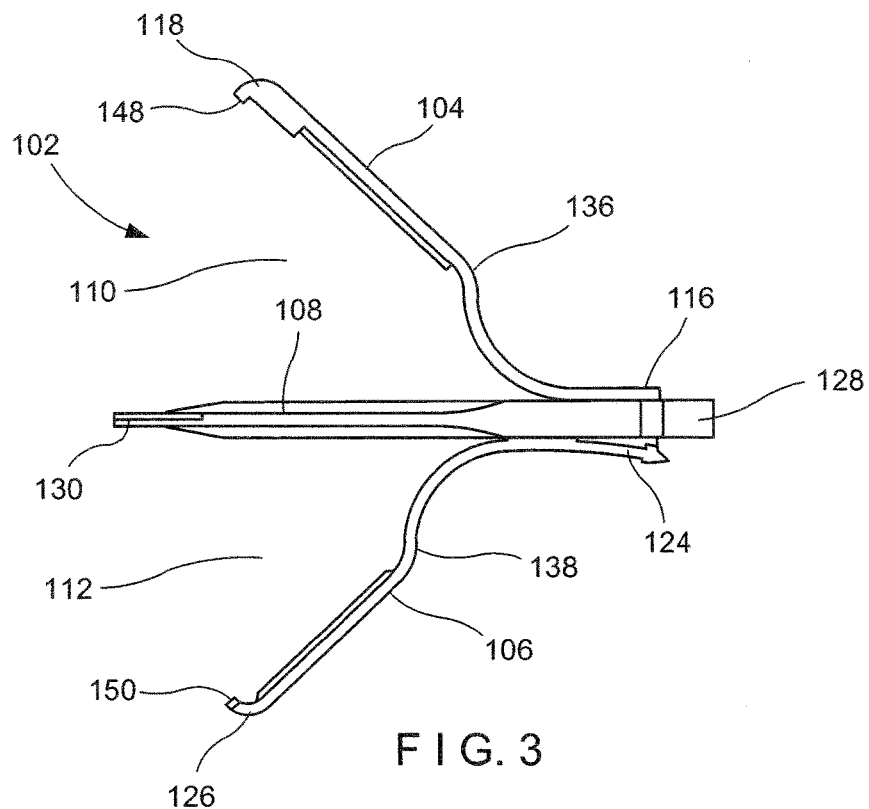
FIG. 3 shows longitudinal side view of a clip of the device of FIG. 1.

The present disclosure may be further understood with reference to the following description and the appended drawings, wherein like elements are referred to with the same reference numerals. The present disclosure is directed to a device for treating tissue and, in particular, to a clip for closing a tissue perforation or defect. Exemplary embodiments of the present disclosure describe a clip having three prongs so that a first portion of tissue along a first side of a tissue defect is gripped in a first space between a first prong and a central prong of the clip and a second portion of tissue along a second side of the tissue defect opposite the first side is gripped in a second space between a second prong and the central prong of the clip. It should be noted that the terms "proximal" and "distal," as used herein, are intended to refer to a direction towards (proximal) and away from (distal) a user (e.g., surgeon) of the device.

As shown in FIGS. 1-5, a device 100 according to a first exemplary embodiment of the present disclosure comprises a clip 102 including a first prong 104, a second prong 106 and a middle prong 108 coupled to one another at proximal ends thereof to define a first space 110 between the first and middle prongs 104, 108 for receiving a first portion of tissue 12 along a first side of a tissue defect 10 and a second space 112 between the second and middle prongs 106, 108 for receiving a second portion 14 of tissue along a second side of the tissue defect 10 opposite the first side. The clip 102 is slidably received within a capsule 114 so that each of the first and second prongs 104, 106 is independently movable between an open configuration in which the first and/or second prongs 104, 106 are spaced apart from the middle prong 108 so that tissue is receivable within one of the first and second spaces 110, 112, and a closed configuration in which the first and/or second prongs 104, 106 are moved toward the middle prong 108 so that tissue received within the first and/or second spaces 110, 112 is gripped between the first and middle prongs 104, 108 or the second and middle prongs 106, 108, respectively. The capsule 114 may be coupled to a handle assembly (not shown) via a sheath having sufficient flexibility to permit insertion of the clip 102 through even along a tortuous path (e.g., through a body lumen) to a target site therewithin. When the device 100 is inserted to the target site the handle assembly remains accessible to a user (e.g., surgeon) so that the handle assembly may be used to move the first and second prongs 104, 106 between the open configurations and the closed configurations.

In particular, the first and second prongs 104, 106 may be biased toward the open configuration so that, when distal ends 118, 126 of the first and second prongs 104, 106 extend distally beyond a distal end 122 of the capsule 114 by a predetermined distance, the first and second prongs 104, 106 move to the open configuration. The first and second prongs 104, 106 are movable relative to the middle prong 108, while the middle prong 108 remains substantially stationary so that, when the clip 102 is drawn proximally into the capsule 114, the first and second prongs 104, 106 are constrained via an interior surface 134 of the capsule 114 toward the middle prong 108 so that they are drawn into the closed configuration. When the first and middle prongs 104, 108 are separated from one another in the open configuration, the first portion of tissue 12 may be received in the first space 110 therebetween. Upon receiving the first portion of tissue 12, the first prong 104 may be moved toward the middle prong 108 so that the first portion of tissue 12 is gripped therebetween. While the first and middle prongs 104, 108 are in the closed configuration, the second prong 106 is still separated from the middle prong 108 in the open configuration so that the second portion of tissue 14 may be received in the second space 112. Upon receiving the second portion of tissue 14, the second prong 108 may be moved toward the closed configuration to grip the second portion of tissue 14 therebetween. When both the first and second prongs 104, 106 are in the closed configuration, the first and second portions of tissue 12, 14 are pressed against the middle prong 108 so that the tissue defect is moved toward a closed position.

The first prong 104 extends from a proximal end 116 engaged to a portion of the middle prong 108 and received within the lumen 120 of the capsule 114 to a distal end 118 which extends distally past a distal end 122 of the capsule 114. The distal end 118 may include a gripping feature 148 extending laterally inward toward the middle prong 108 to facilitate a gripping of tissue received within the first space 110. Similarly, the second prong 106 extends from a proximal end 124 engaged to a portion of the middle prong 108 and received within the lumen 120 to a distal end 126 which extends distally past the distal end 122 of the capsule 114. The second prong 106 according to this embodiment also includes a gripping feature 150 extending laterally inward toward the middle prong 108 for gripping tissue received therebetween. The first and second prongs 104, 106 may be substantially diametrically opposed from one another about the middle prong 108. Proximal ends 116, 124 of the first and second prongs 104, 106 may be connected to one another via, for example, a C-shaped connection which encircles the middle prong 108 to prevent interference therewith. The first prong 104 may also include a first engaging tab 152 extending radially outward from the proximal end 116 thereof for engaging a portion the capsule 114. Since the first and second prongs 104, 106 are connected to one another, the engagement between the first engaging tab 152 and the capsule 114 locks both the first and second prongs 104, 106 relative to the capsule 114, in the closed configuration. The proximal end 116 of the first prong 104 may also include a second engaging tab 154 extending radially inward to engage a portion of the middle prong 108. Although the first prong 104 is described and shown as including the first and second engaging tabs 152, 154, in another embodiment, the second prong 106 may include the first and second engaging tabs 152, 154 for engaging the capsule 114 and the middle prong 108, respectively. In an alternate embodiment, the first and second prongs 104, 106 may not be connected to one another so that each of the first and second prongs 104, 106 include both the first engaging tab 152 and the second engaging tab 154 at the proximal ends 116, 124 thereof for engaging corresponding portions of the capsule 114 and the middle prong 108, respectively.

The middle prong 108 extends along a substantially straight line from a proximal end 128 connected to a control element 132 and received within the lumen 120 to a distal end 130. The control element 132 extends from a distal end 140 connected to the middle prong 108 to a proximal end within the handle assembly so that, when the device 100 is inserted to a target site within the patient's body, the control element 132 may be moved longitudinally relative to the capsule 114 to control a movement of the first and second prongs 104, 106 between the open configurations and the closed configurations. The proximal end 128 of the middle prong 108 according to this embodiment includes a recess 156. The recess 156 is sized and shaped to receive the second engaging tab 154 of the first prong and/or second prongs 104, 106.

The capsule 114 extends longitudinally from a proximal end 158 to the distal end 122 and includes the lumen 120 extending longitudinally therethrough from the proximal end 158 to the distal end 122. The lumen 120 is sized and shaped to slidably receive the clip 102 therein so that when the clip 102 is drawn proximally thereinto, the first and second prongs 104, 106 are constrained via the interior surface 134. The capsule 114 according to this embodiment includes a window 160 extending laterally through a proximal portion thereof for receiving the first engaging tab 152 at one of the proximal ends 116, 124 of the first and second prongs 104, 106, when the first and second prongs 104, 106 are locked relative thereto. The window 160 may be formed via a tab 162 cut through a wall of the capsule 114 and bent radially inward toward a center axis of the capsule 114. After both the first and second prongs 104, 106 have been moved to the closed configurations, the clip 102 may be drawn even further proximally until the proximal end 116 of the first prong 104 engages the tab 162. The tab 162 and the proximal end 116 of the first prong 104 engage one another in a sliding fashion so that the proximal end 116 is moved radially outward away from a centerline of the capsule 114. Thus, engagement between the tab 162 and the proximal end 116 causes the first engaging feature 152 to engage the windows 160 while the second engaging feature 154 is simultaneously disengaged from the recess 156 of the middle prong 108, permitting the middle prong 108 to be entirely withdrawn from the clip 102. Upon withdrawal of the middle prong 108, the first and second portions of tissue 12, 14 previously gripped thereagainst are gripped between the first and second prongs 104, 106, holding the tissue defect in the closed configuration.

The first and second prongs 104, 106 according to this embodiment are biased toward the open configurations so that distal ends 118, 126 of the first and second prongs 104, 106, respectively, are separated from the distal end 130 of the middle prong 108 until the clip 102 is drawn proximally relative to the capsule 114 via the control element 132 into the lumen 120. When the clip 102 is drawn into the capsule 114 by a first distance, the first prong 104 is constrained toward the closed configuration via contact with an interior surface 134 of the capsule 114. When the clip 102 is drawn farther proximally relative to the capsule 114 by a second distance, the second prong 106 is constrained toward the closed configuration via contact with the interior surface 134 of the capsule 114.

In one embodiment, the first and second prongs 104, 106 are independently movable between the open and closed configurations via first and second shoulders 136, 138 extending along portions of the first and second prongs 104, 106, respectively. The first shoulder 136 extends along a portion of the first prong 104 so that, when the first shoulder 136 is received within the capsule 120, the first shoulder 136 engages the interior surface 134 of the capsule 114 to move the first prong 104 toward the closed configuration. The second shoulder 138 extends along a portion of the second prong 106, distal of the first shoulder 136 so that, when the second shoulder 138 is received within the capsule 114, the second shoulder 138 engages the interior surface 134 of the capsule 114 to move the second prong 106 toward the closed configuration. The staggered positions of the first and second shoulders 136, 138 facilitates moving of the first prong 104 toward the closed configuration prior to the movement of the second prong 106 toward the closed configuration. The first and second shoulders 136, 138 may be any change in geometry of the first and second prongs 104, 106 such as, for example, a bend, a bulge, a raised and/or lowered flange, or a protrusion, which, when staggered along the lengths of the first and second prongs 104, 106, would cause the first and second prongs 104, 106 to be constrained via the interior surface 134 of the capsule 114 independently of one another.

Figure 4:
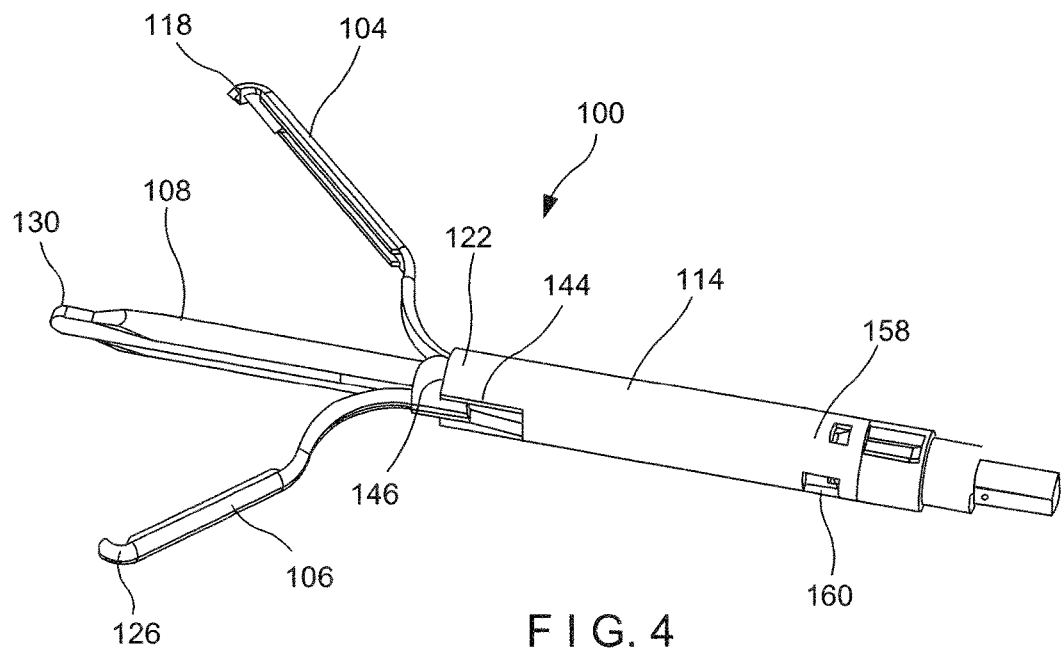
FIG. 4 shows another perspective view of the device of FIG. 1.

As shown in FIG. 4, the capsule 114 may also include a staggered opening 146 to facilitate independent movement of the first and second prongs 104, 106 between the open and closed configurations. For example, the distal end 122 of the capsule 114 may include a recess 144 extending proximally therefrom on a side of the capsule 114 in which the second prong 106 is received and engaged. Thus, the control member 132 must be moved even further proximally relative to the capsule 114 before the second shoulder 138 of the second prong 106 engages the interior surface 134 of the capsule 114 to be moved toward the closed configuration.

Figure 5:
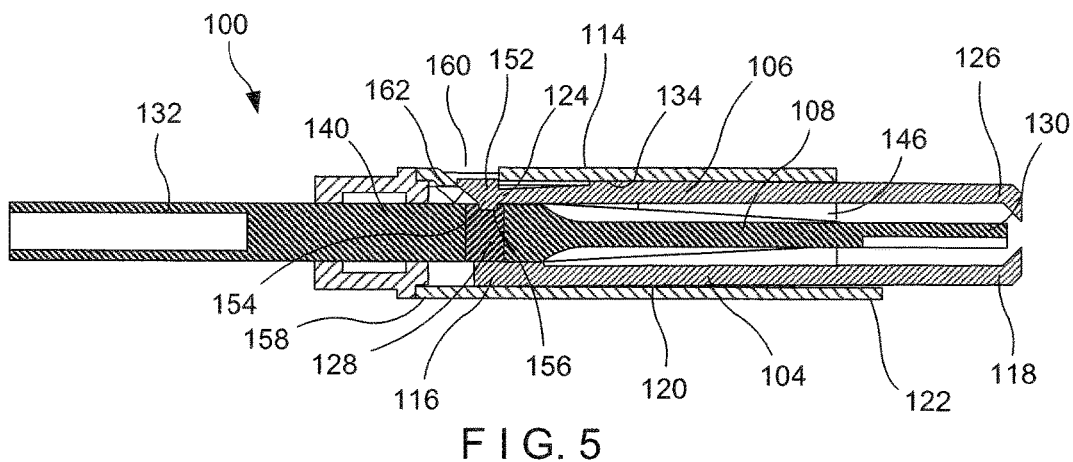
FIG. 5 shows a longitudinal cross-sectional view of the device of FIG. 1.

The control element 132 according to this embodiment is longitudinally movable relative to the capsule 114 through four ranges of motion. In a first range of motion, the control element 132 is moved proximally relative to the capsule 114 by the first distance to move the first prong 104 from the open configuration to the closed configuration. The control element 132 is moved within this first range of motion move the first prong 104 relative to the middle prong 108 between the open and closed configurations, as desired. In a second range of motion, the control element 132 is moved further proximally relative to the capsule 114 by the second distance to move the second prong 106 from the open configuration to the closed configuration. The control element 132 may be moved within this second range of motion to move the second prong 106 relative to the middle prong 108 between the open and closed configurations, as desired. The first and second distances are defined by a distance between the first and shoulders 136, 138 and a distal edge of the capsule 114 meeting each of the first and second shoulders 136, 138. Once both the first and second prongs 104, 106 have been moved to the closed configuration, the control element 132 may be drawn further proximally relative to the capsule 114, within a third range of motion, as shown in FIG. 5, until the proximal ends 116, 124 of the first and second prongs 104, 106 engage the tabs 162 at the proximal end 152 of the capsule 114 to simultaneously release the middle prong 108 therefrom and locking the first and second prongs 104, 106 to the capsule. Once the middle prong 108 has been released, the control element 132 may be moved farther proximally, through a fourth range of motion, to draw the middle prong 108 from the clip 102, activating a decoupling of the capsule 114 from the sheath 164, leaving the clip 102 deployed in the patient body. The capsule 114 may be decoupled from the sheath 164, deploying the clip 102 in the body, via any of a variety of known deployment mechanisms. For example, a portion of the middle prong 108 or the control element 132 may abut a coupling feature (e.g., a bushing) between the capsule 114 and the sheath 164 to disengage the capsule 114 therefrom.

Figure 6:
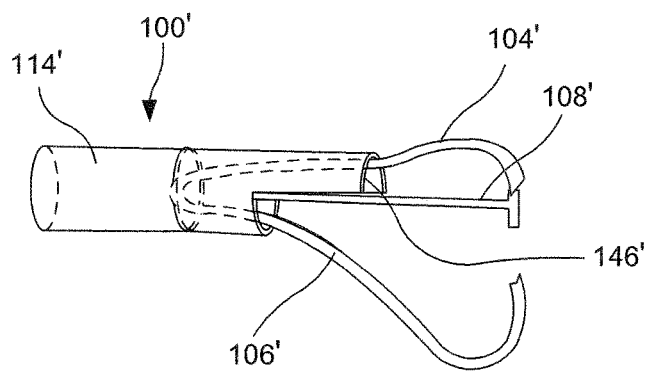
FIG. 6 shows a longitudinal side view of a device according to an alternate embodiment of the present disclosure.

Although, the device 100 is described and shown as including both the staggered first and second shoulders 136, 138 and the staggered distal opening 146, a device according to the present disclosure may include only one of those features. For example, as shown in FIG. 6, a device 100' may comprise a capsule 114' including a staggered distal opening 146' so that, upon drawing first, second and middle prongs 104', 106', 108' proximally into the capsule 114', the first prong 104' is moved from a open configuration toward a closed configuration prior to the second prong 106'. Although the distal opening 146' of the capsule 114' is staggered, the first and second prongs 104', 106' according to this embodiment are substantially symmetrical about a longitudinal axis of the device 100'—e.g., the first and second prongs 104', 106' do not include staggered shoulders along lengths thereof. Similarly, a device according to the present disclosure may include staggered first and second shoulders along first and second prongs, respectively, and a non-staggered distal opening at the distal end of the capsule.

According to an exemplary method of use of the device 100, the clip 102 is inserted through, for example, a working channel of an endoscope, to a target site within a patient's body. The clip 102 is inserted to the target site with both the first and second prongs 104, 106 in the closed configuration. Upon arrival at the target site, the clip 102 is moved distally relative to the capsule 114 a predetermined distance such that both the first and second prongs 104, 106 move to the open configuration, defining the first and second spaces 110, 112. The clip 102 is moved over the tissue defect so that the first portion of tissue 12 is received in the first space 110 between the first prong 104 and the middle prong 108. The clip 102 is then drawn proximally relative to the capsule 114 via the control element 132 until the first shoulder 136 contacts the interior surface 134 of the capsule 114, moving the first prong 104 toward the middle prong 108 to the closed configuration to grip the first portion of tissue 12 therebetween. The control element 132 is movable within this first range of motion to move the first prong 104 between the open and closed configurations until the first portion of tissue 12 is gripped between the first prong 104 and the middle prong 108, as desired.

Once the first portion of tissue 12 has been gripped, as desired, the clip 102 is moved toward the second portion of tissue 14 so that the second portion of tissue 14 is received within the second space 112. The clip 102 is then moved proximally relative to the capsule 114 via the control element 132 until the second shoulder 138 contacts the interior surface 134 of the capsule 114 to move the second prong 106 toward the middle prong 108—i.e., toward the closed configuration. The control element 132 is moved within this second range of motion to grip the second portion of tissue 14 between the second prong 106 and the middle prong 108, as desired. Once both the first and second prongs 104, 106 are in the closed configuration, the control element 132 is moved farther proximally within a third range of motion to simultaneously disengage the first and second prongs 104, 106 from the middle prong 108 and cause the first engaging feature 152 at the proximal end 116 of the first prong 104 to engage the window 160. Thus, the first and second prongs 104, 106 are locked in the closed configuration within the capsule 114. The control element 132 may then be moved further proximally relative to the capsule 114 to withdraw the middle prong 108 therefrom and deploy the clip 102 at the target site. Withdrawal of the middle prong 108 causes the first and second portions of tissue 12, 14, which were previously gripped against the middle prong 108, to be gripped between the first and second prongs 104, 106 against one another to facilitate tissue healing therebetween.

Figure 7:
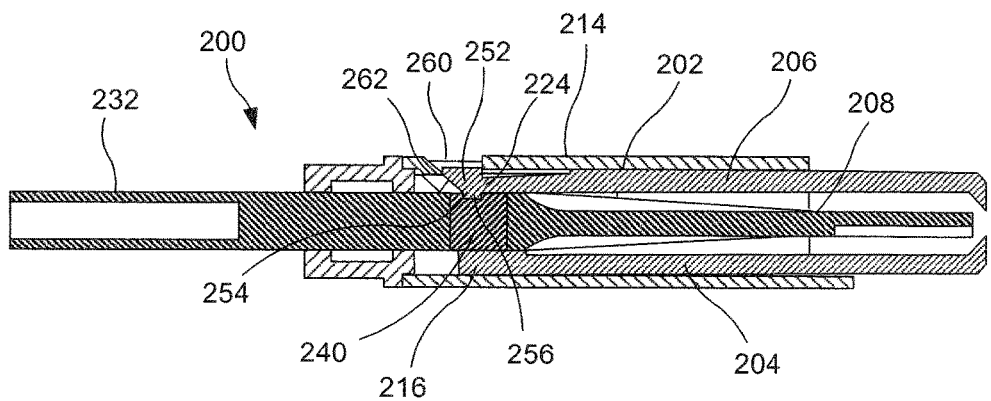
FIG. 7 shows a longitudinal cross-sectional view of a device according to a second exemplary embodiment of the present disclosure.

As shown in FIG. 7, a device 200 according to another exemplary embodiment is substantially similar to the device 100, comprising a clip 202 including a first prong 204, a second prong 206 and a middle prong 208 such that a first portion of tissue may be received and gripped between the first prong 204 and the middle prong 208 and a second portion of tissue may be received and gripped between the second prong 206 and the middle prong 208. The clip 202 is movable within a capsule 214, via a control element 232, through a first range of motion moving the first prong 204 relative to the middle prong 208 between an open configuration and a closed configuration, and a second range of motion moving the second prong 206 relative to the middle prong 208 between an open configuration and a closed configuration. Similarly to the clip 102, one of proximal ends 216, 224 of the first and second prongs 204, 206 includes a first engaging tab 252 extending laterally outward to engage a portion of the capsule 214 in a locked configuration, and a second engaging tab 254 extending laterally inward. The second engaging tab 254, however, does not engage a portion of the middle prong 208 so that the middle prong 208 may be withdrawn therefrom. Rather, the middle prong 208 is fixedly connected to the first and second prongs 204, 206 so that the middle prong 208 is not withdrawable from the clip 202. The control element 232 is instead releasably coupled to the clip 202. For example, a distal end 240 of the control element 232 includes a recess 256 sized and shaped to receive the second engaging tab 254. Thus, when the control element 232 is moved through the third range of motion, the proximal end 216 of the first prong 204 engage tab 262 of the capsule 214, causing the first engaging tab 252 to engage the window 260 along a proximal portion of the capsule 214 while simultaneously disengaging the second engaging tab 254 from the recess 256 of the control element 232. Thus, the control element 232 is released from the clip 202 and withdrawn therefrom, while leaving the middle prong 208 intact within the clip 202. Thus, the first and second portions of tissue remain gripped against the middle prong 208 via the first and second prongs 204, 206. The middle prong 208 may be formed of a bioabsorbable material so that, upon deployment of the clip 202 within the body, the middle prong 208 may dissolve, aiding in healing between the first and second portions of tissue.

Figure 8:
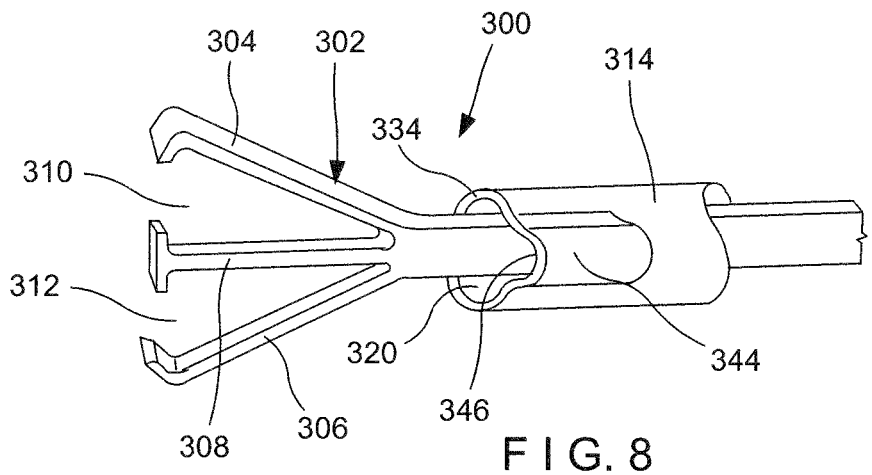
FIG. 8 shows a perspective view of a device according to a third exemplary embodiment of the present disclosure.
Figure 9:
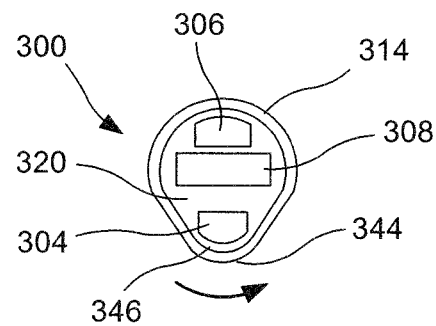
FIG. 9 shows a plan view from a distal end of the device of FIG. 8.

As shown in FIGS. 8 and 9, a device 300 according to another exemplary embodiment of the present disclosure is substantially similar to the devices 100, 200 described above, comprising a clip 302 including a first prong 304, a second prong 306 and a middle prong 308 movably received within a capsule 314 so that the first and second prongs 304, 306 are independently movable toward and away from the middle prong 308 between open and closed configurations. Rather than being independently movable between the open and closed configurations via a staggered shoulder along the first and second prongs 304, 306 or a staggered distal opening of the capsule 314, the first and second prongs 304, 306 are independently moved via rotation of the capsule 314 relative to the clip 302 about a longitudinal axis of the device 300. The capsule 314 is sized and shaped to define a lumen 320 extending therethrough. A distal portion of the capsule 314 is shaped to include a protrusion 344 so that a corresponding enlarged portion 346 of the lumen 320 is specifically sized and shaped to permit one of the first and second prongs 304, 306 to be received therein in the open configuration. The middle prong 308 is sized to be prevented from being received within the enlarged portion 338 of the lumen 320 so that when one of the first and second prongs 304, 306 is received within the enlarged portion 338 to be moved toward the open configuration, the other of the first and second prongs 304, 306 is constrained via an interior surface 334 of the capsule 314 toward the closed configuration. Rotation of the capsule 314 approximately 90 degrees about a longitudinal axis thereof so that neither of the first and second prongs 304, 306 is received within the enlarged portion 338, constrains both of the first and second prongs 304, 308 toward the closed configurations. Rotation of the capsule 314 another 90 degrees about the longitudinal axis—i.e., 180 degrees from the initial configuration in which one of the first and second prongs 304, 306 was received in the enlarged portion 346—permits the other of the first and second prongs 304, 306 to be received in the enlarged portion 338 and moved to the open configuration.

For example, upon insertion of the clip 302 to a target site within a patient body, the capsule 314 is rotated relative to the clip 302 about the longitudinal axis such that the first prong 304 is received within the enlarged portion 346 of the lumen 320 so that the first prong 304 is separated from the middle prong 308 toward the open configuration. A first portion of tissue is received within a first space 310 between the first prong 304 and the middle prong 308. Once the first portion of tissue has been received in the first space 310, the capsule 314 is rotated approximately 180 degrees about the longitudinal axis, moving the first prong 304 toward the closed configuration and receiving the second prong 306 in the enlarged portion 338 so that the second prong 306 is moved from the closed configuration to the open configuration. A second portion of tissue is then received within a second space 312 between the second prong 306 and the middle prong 308. Rotation of the capsule approximately 90 degrees about the longitudinal axis constrains both the first and second prongs 304, 306 toward the closed configuration so that the first and second portions of tissue, respectively, are gripped against the middle prong 308.

Figure 10:
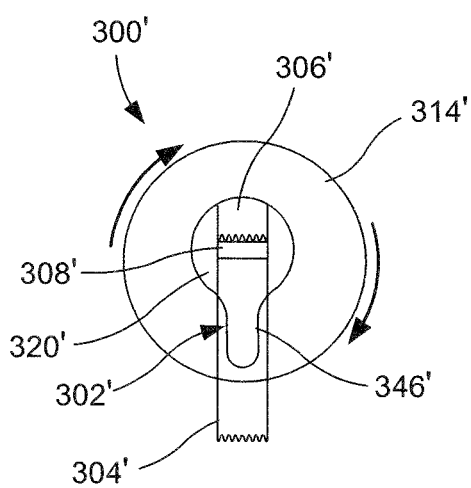
FIG. 10 shows a plan view from a distal end of a device according to an alternate embodiment of the present disclosure, in a first configuration.
Figure 11:
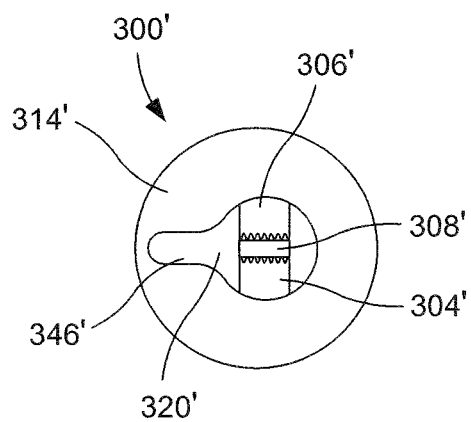
FIG. 11 shows a plan view from the distal end of the device, in a second configuration.

As shown in FIGS. 10 and 11, a device 300' is substantially similar to the device 300, described above. Rather than a protrusion in a capsule 314' forming a corresponding enlarged portion in a lumen 320' thereof, however, an exterior of the capsule 314' may be substantially cylindrical, free of protrusions. Instead, a distal portion of the lumen 320' includes a recess 346' extending along a portion thereof, the recess 346' specifically sized to receive one of a first and second prong 304', 306' of a clip 302' in an open configuration, but preventing a middle prong 308' from being received therein so that the other of the first and second prongs 304', 306' is constrained in a closed configuration. Similarly to the device 300, the capsule 314' is rotatable about a longitudinal axis of the device 300' relative to the clip 302' to independently move the first and second prongs 304', 306' between open and closed configurations.

Figure 12:
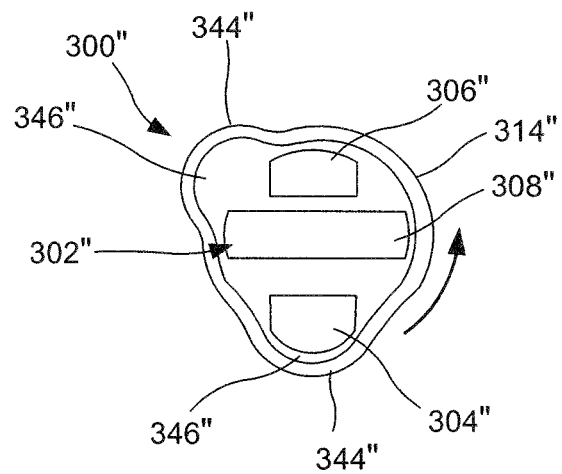
FIG. 12 shows a plan view from a distal end of a device according to another alternate embodiment of the present disclosure.

According to an alternate embodiment, as shown in FIG. 12, a capsule 314" of a device 300" includes more than one enlarged portion 344" for receiving one of a first and second prong 304", 306" of a clip 302" in an open configuration, while preventing a middle prong 308" from being received therein, so that the capsule 314" is not required to be rotated 180 degrees relative to the clip 302" about a longitudinal axis of the device 300". Enlarged portions 346", however, should be separated from one another about a circumference of the capsule 314' by a distance sufficient to constrain both the first and second prongs 304", 306" in a closed configuration when received therebetween.

Figure 13:
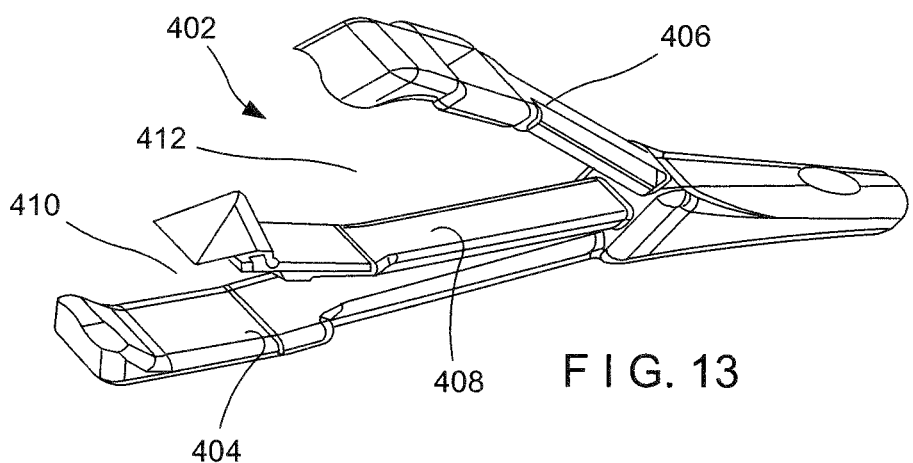
FIG. 13 shows a perspective view of a device according to a fourth exemplary embodiment of the present disclosure.

As shown in FIG. 13, a clip 402 is substantially similar to the clips 102-302 described above, comprising a first prong 404, a second prong 406 and a middle prong 408. While middle prongs of the above clips are described as being substantially stationary relative to the first and second prongs, the middle prong 408 is laterally movable relative to the first and second prongs 404, 406 such that a first space 410 defined between the first and middle prongs 404, 408 and a second space 412 defined between the second and middle prongs 406, 408 is adjustable via movement of the first and second prongs 404, 406 and the middle prong 408. For example, upon receiving a first portion of tissue in the first space 410 between the first and middle prongs 404, 408, the middle prong 408 may be moved toward the first prong 404 to close the first space 410 and grip the first portion of tissue therebetween. A second portion of tissue may then be received within the second space 412 between the second prong 406 and the middle prong 408. Once the second portion of tissue has been received within the second space 412, as desired, the second prong 406 is moved toward the middle prong 408 to close the second space 412 and grip the second portion of tissue therebetween.

Figure 14:
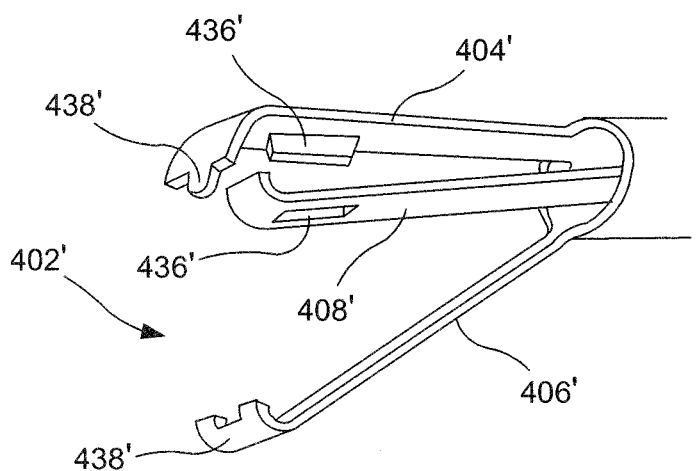
FIG. 14 shows a perspective view of a device according to a further exemplary embodiment of the present disclosure.

In a further embodiment, as shown in FIG. 14, a clip 402' is substantially similar to the clip 402 described above. The clip 402', however, further includes a first locking mechanism 436' for locking a middle prong 408' to a first prong 404' in a closed configuration and a second locking mechanism 438' for locking a second prong 406' to one of the first prong 404' and the middle prong 408'. The first and second locking mechanisms 436', 438' may include one of a latch, slide bar and a tubular cinch. The first and second locking mechanisms 436', 438' may also include tissue piercing elements.

Figure 15:
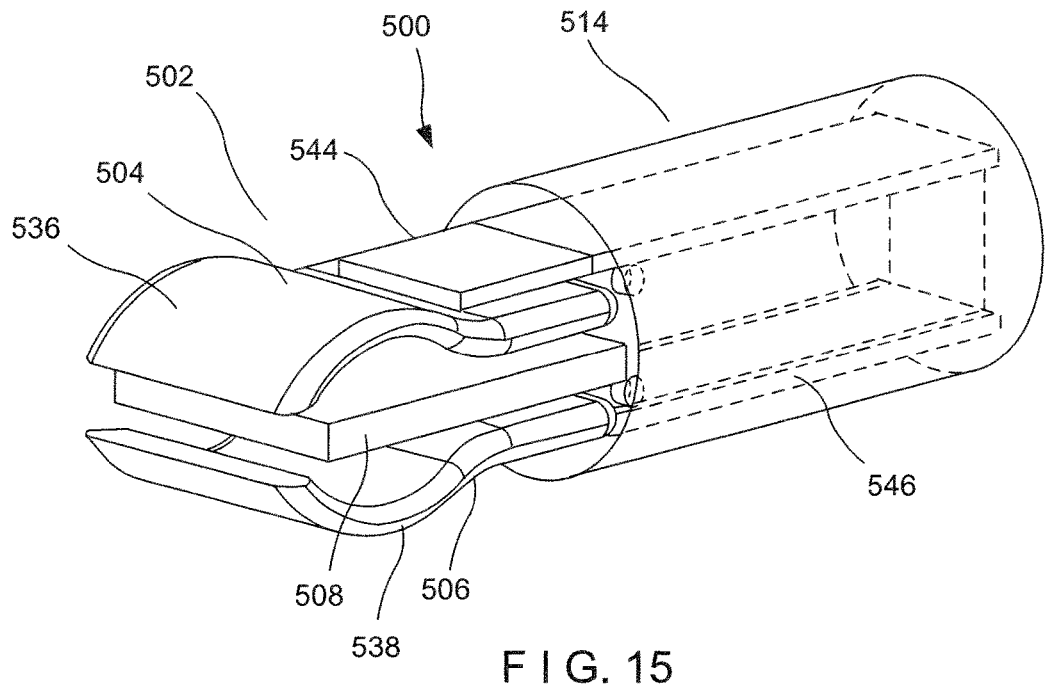
FIG. 15 shows a perspective view of a device according to a fifth exemplary embodiment of the present disclosure.
Figure 16:
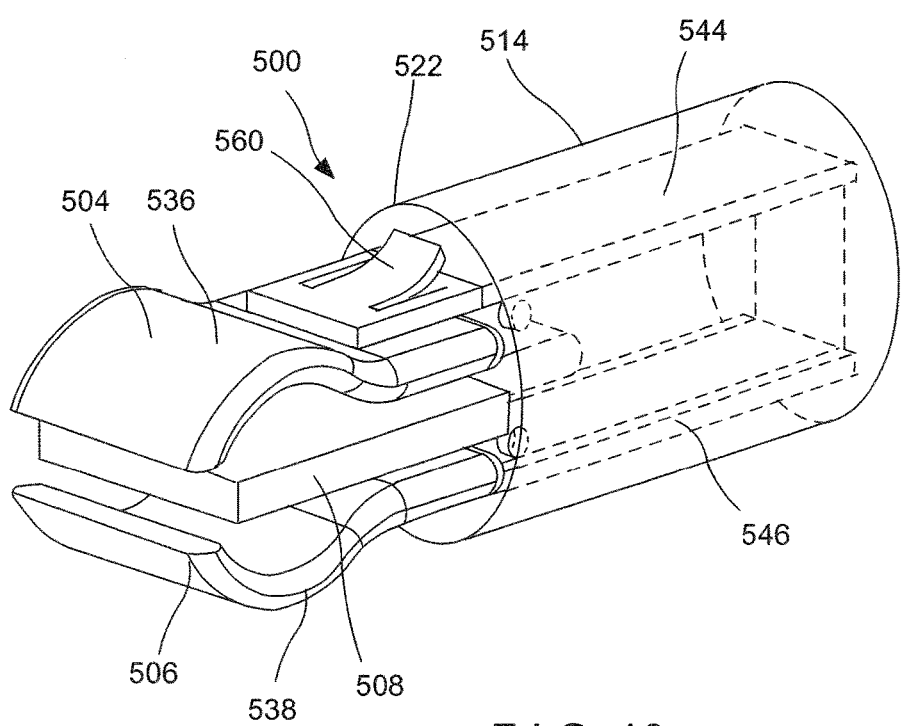
FIG. 16 shows another perspective view of the device of FIG. 15.

As shown in FIGS. 15 and 16, a device 500 is substantially similar to the devices 100 and 200 described above, comprising a clip 502 including a first prong 504, a second prong 506 and a middle prong 508, proximal ends of which are housed within a capsule 514. Similarly to the devices 100, 200, the first and second prongs 504, 506 are independently movable between open configurations, in which the first and second prongs 504, 506 are separated from the middle prong 508, and closed configurations, in which the first and second prongs 504, 506 are moved toward the middle prong to grip a tissue thereagainst. Movement of the first and second prongs 504, 506 toward and away from the middle prong 508, however, is actuated by first and second actuating elements 544, 546 which interface with the first and second prongs 504, 506, respectively. The first actuating element 544 is slidably received within the capsule 514 and longitudinally movable relative to the clip 502 such that when the first actuating element 536 is moved distally over a distal portion of the first prong 504, the first actuating element 544 engages a curved exterior 536 thereof to move the first prong 504 toward the middle prong 508. The first actuating element 544 may be moved distally and proximally relative to the first prong 504 to move the first prong 504 between the closed and open configurations, respectively, until tissue is received and gripped thereby against the middle prong 508 as desired. Similarly, the second actuating element 546 is longitudinally slidable within the capsule 514 so that, when the second actuating element 546 is moved distally over a distal portion of the second prong 506, the second actuating element 546 engages a curved exterior 538 of the second prong 506 to move the second prong toward the middle prong 508. The second actuating element 546 may be moved distally and proximally relative to the second prong 506 to move the second prong between the closed and open configurations, respectively, until tissue is received and gripped thereby against the middle prong 508 as desired.

The first and second actuating elements 544, 546 are independently actuated via a handle assembly coupled to a proximal end of the device 500. The first and second actuating elements 544, 546 according to this embodiment include a frangible or releasable coupling distal of the handle assembly so that, upon moving both the first and second prongs 504, 506 to the closed configurations, distal portions of the first and second actuating elements 544, 546 and the capsule 514 may be deployed in a patient body. As shown in FIG. 16, each of the first and second actuating elements 544, 546 may also include a locking element 560 along a portion thereof. The locking element 560 may, for example, include a laterally outwardly biased member (e.g., tab) which, when moved distally beyond a distal end 522 of the capsule 514, engages the distal end 522, preventing the first and second actuating elements 544, 546 from being proximally movable relative to the clip 502 and thereby locking the first and second prongs 504, 506 against the middle prong 508 in the closed configurations.

Figure 17:
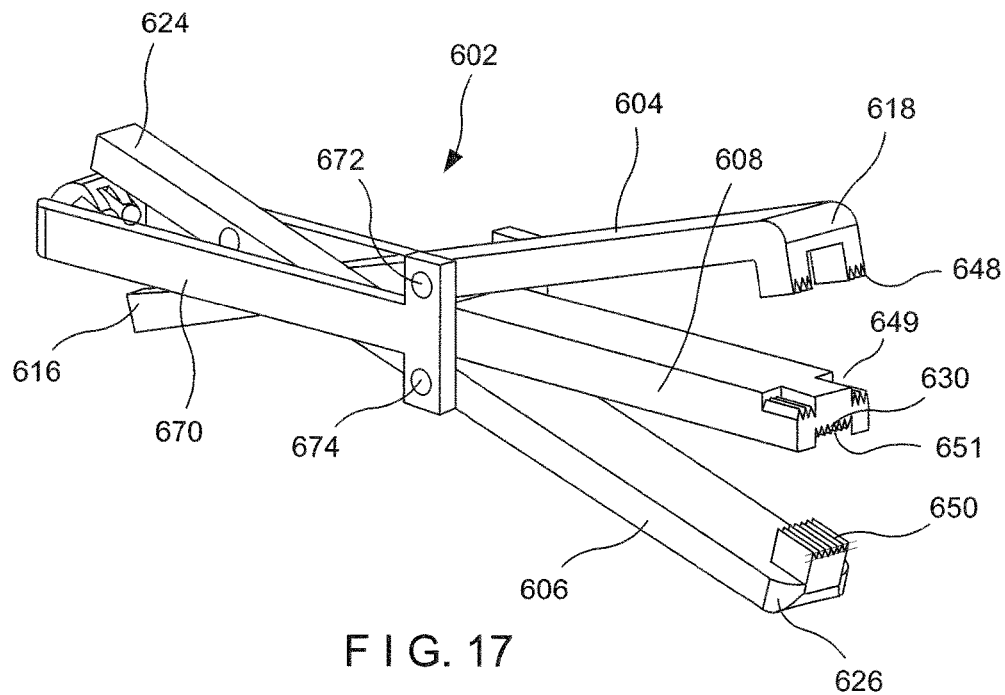
FIG. 17 shows a perspective view of a device according to a sixth exemplary embodiment of the present disclosure, in a first configuration.
Figure 18:
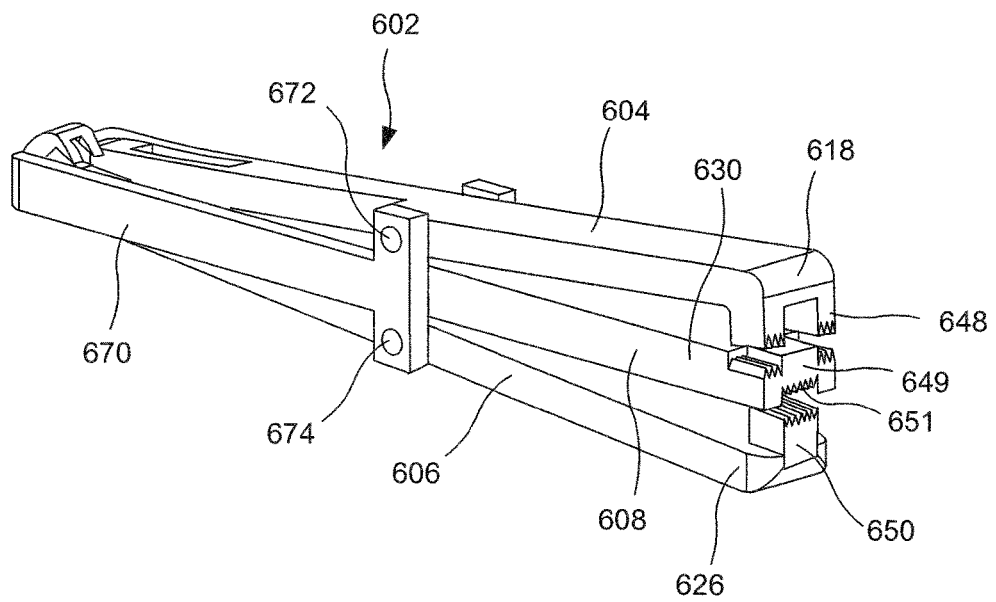
FIG. 18 shows a perspective view of the device of FIG. 17, in a second configuration.

As shown in FIGS. 17 and 18, a clip 602 is substantially similar to the clips 102-502 described above, comprising a first prong 604, a second prong 606 and a middle prong 608. The first, second and middle prongs 604, 606, 608, however, are coupled to one another in a substantially scissor-like fashion. In particular, the clip 602 further includes a connecting element 670 connecting the first, second and middle prongs 604, 606, 608 to one another. While the middle prong 608 is fixedly connected to the connecting element 670, the first and second prongs 604, 606 are pivotally coupled thereto at a first pivoting point 672 and a second pivoting point 674, respectively. The first and second prongs 604, 606 are coupled to first and second control elements, respectively, which are independently actuatable via a handle assembly connected to proximal ends thereof to independently move the first and second prongs 604, 606 toward and away from the middle prong 608 between closed and open configurations. Although not shown, the clip 602 may be received within a capsule, substantially similar to the capsule 114, described and shown with respect to the device 100.

The first prong 604 is pivotable about the first pivoting point 672 between an open configuration, in which a distal end 618 is separated from a distal end 630 of the middle prong 608 to receive a tissue therebetween, and a closed configuration, in which the distal end 618 is moved toward the distal end 630 to grip the tissue therebetween. The first control element according to this embodiment is releasably coupled to a proximal end 616 of the first prong 604 to move the first prong 604 between the open and closed configurations. In particular, the first control element may be drawn proximally relative to the clip 602 to move the first prong 604 toward the closed configuration. Drawing the first control element farther proximally beyond a predetermined threshold level disengages the first control element from the first prong 604 so that the clip 602 may be deployed in the patient's body.

Similarly, the second prong 606 is pivotable about the second pivoting point 674 between an open configuration (shown in FIG. 17), in which a distal end 626 of the second prong is separated from the distal end 630 of the middle prong 608 to receive a tissue therebetween, and a closed configuration (shown in FIG. 18), in which the distal end 626 is moved toward the distal end 630 to grip tissue therebetween. The second control element may be releasably coupled to a proximal end 624 of the second prong 606 to move the second prong 606 between the open and closed configurations. In particular, the second control element may be drawn proximally relative to the clip 602 to move the second prong 606 toward the closed configuration. Drawing the second control element even farther proximally beyond a predetermined threshold level may disengage the second control element from the first prong 606 so that the clip 602 may be deployed in the patient's body.

As described above, the clip 602 is received within a capsule, locking the first and second prongs 604, 606 in the closed configuration. In another embodiment, distal ends 618, 626 of the first and second prongs 604, 606 include tissue gripping features in the form of prongs 648, 650, respectively, which engage corresponding portions 649, 651 at the distal end 630 of the middle prong 608 to interlock therewith. one another when the first and second prongs 604, 606 are moved to the closed configuration. The prongs 648, 650 and the corresponding portions 649, 651 of the middle prong 608 may include, for example, teeth, ridges or protrusions therealong for facilitating a gripping of tissue received therebetween.

Figure 19:
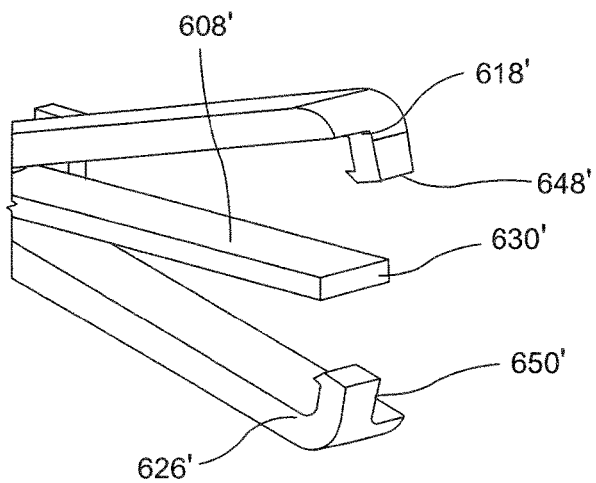
FIG. 19 shows a perspective view of an alternate gripping feature for the device of FIG. 17.
Figure 20:
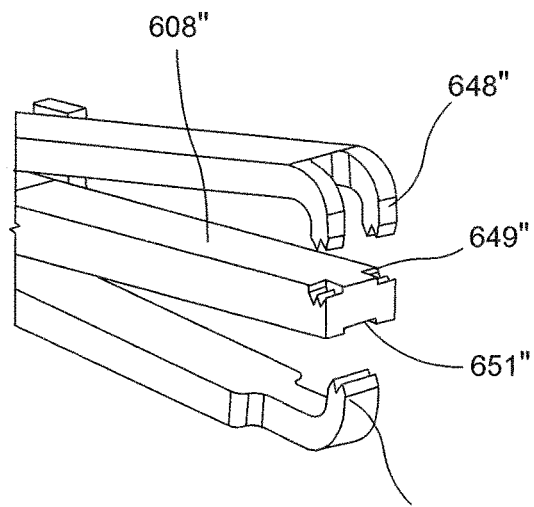
FIG. 20 shows a perspective view of another alternate gripping feature for the device of FIG. 17.
Figure 21:
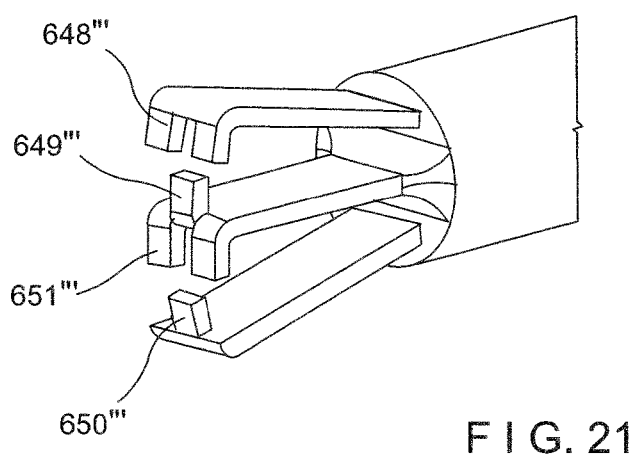
FIG. 21 shows a perspective view of yet another alternate gripping feature for the device of FIG. 17.

The clip 602, however, may include any of a variety of gripping features such as, for example, latching barbs (as shown in FIG. 19), in which distal ends 618', 626' of first and second prongs 604', 606' include a first and second latch 648', 650', respectively, which when the first and second prongs 604', 606' are moved toward a middle prong 608' in a closed configuration, latch over a distal end 630' of the middle prong 608'. In another embodiment, as shown in FIG. 20, the gripping feature includes interlocking prongs 648", 650" which engage corresponding portions 649", 651" of a middle prong 608" and also interlock with one another. In another embodiment, as shown in FIG. 21, interlocking prongs 648''', 650''' and corresponding portions 649''', 651''' are substantially similar to the embodiment shown and described in regard to FIGS. 19 and 20, but do not include any additional gripping features therealong such as, for example, teeth, ridges or protrusions.

While embodiments have been described above, a number of modifications and changes may be made without departing from the scope of the disclosure. Thus, it is intended that the present disclosure cover modifications and variations provided that they come within the scope of the appended claims and their equivalents.

What is claimed is:

1. A device for treating tissue, comprising:
   a capsule extending longitudinally from a proximal end to a distal end and including a lumen extending therein; and
   a clip slidably received within the lumen of the capsule, the clip including:
      a middle prong;
      a first outer prong coupled to the middle prong so that the first prong is movable relative to the middle prong between a first open configuration, in which distal ends of the first and middle prongs are separated from one another to receive a first portion of tissue therebetween, and a first closed configuration, in which the distal end of the first prong is moved toward the distal end of the middle prong to grip the first portion of tissue therebetween; and
      a second outer prong coupled to the middle prong so that the second prong is movable relative to the middle prong between a second open configuration, in which distal ends of the second and middle prongs are separated from one another to receive a second portion of tissue therebetween, and a second closed configuration, in which the distal end of the second prong is moved toward the distal end of the middle prong to grip the second portion of tissue therebetween, the first and second outer prongs independently movable relative to the middle prong to be moved between the first and second open configurations to the first and second open configurations and the first and second closed configurations, wherein the first and second prongs are biased toward the first and second open configurations, respectively, so that, when the clip is drawn proximally into the capsule, the first and second prongs are constrained toward the first and second closed configurations via an interior surface of the capsule,
      wherein the middle prong is releasably coupled to the first and second prongs.

2. The device of claim 1, wherein one of the first and second prongs includes an engaging element for engaging a corresponding engaging element of the capsule when the middle prong is disengaged therefrom to lock the first and second prongs within the capsule in the first and second closed configurations.

3. The device of claim 1, wherein the first prong includes a first shoulder positioned therealong so that, when the first shoulder engages the interior surface of the capsule the first prong is constrained toward the first closed configuration, and the second prong includes a second shoulder positioned therealong so that, when the second shoulder engages the interior surface of the capsule the second prong is constrained toward the second closed configuration, the second shoulder positioned distally of the first shoulder so that when the clip is moved proximally relative to the capsule, the clip is moved to the first closed configuration prior to the second closed configuration.

4. The device of claim 1, wherein the distal end of the capsule includes a longitudinal recess extending therealong, the recess aligned with the second prong so that, when the clip and the capsule are moved longitudinally relative to one another toward the first and second closed configurations, the first prong engages the interior surface of the capsule before the second prong.

5. The device of claim 1, further comprising a control element coupled to the proximal end of the middle prong for moving the clip between the first and second open configurations and the first and second closed configurations.

6. The device of claim 5, wherein the control element is releasably coupled to the middle prong.

7. The device of claim 1, wherein the lumen of the capsule includes an enlarged portion at a distal end therefrom, the enlarged portion sized and shaped to receive one of the first and second prongs in one of the first and second open configurations, respectively, and to prevent receipt of the middle prong therein, the capsule rotatable about a longitudinal axis thereof relative to the clip to move the clip between the first and second open configurations and the first and second closed configurations.

8. The device of claim 1, wherein distal ends of at least one of the first, second and middle prongs include tissue gripping structures.

9. The device of claim 1, wherein the first, second and middle prongs are connected to one another via a connecting element, the middle prong fixed relative to the connecting element, the first prong pivotally coupled thereto via a first pivoting point and the second prong pivotally coupled thereto via a second pivoting point.

10. The device of claim 9, wherein a proximal end of the first prong is connected to a first control member and a proximal end of the second prong is connected to a second control member, the first and second control members being independently actuatable.

* * * * *